United States Patent [19]

Miller

[11] Patent Number: 5,331,002
[45] Date of Patent: Jul. 19, 1994

[54] 5-ARYL-4-ALKYL-3H-1,2,4-TRIAZOLE-3-THIONES USEFUL AS MEMORY ENHANCERS

[75] Inventor: Jerry A. Miller, Cincinnati, Ohio

[73] Assignee: Merrell Dow Pharmaceuticals Inc., Cincinnati, Ohio

[21] Appl. No.: 105,693

[22] Filed: Aug. 11, 1993

Related U.S. Application Data

[60] Division of Ser. No. 832,062, Feb. 6, 1992, Pat. No. 5,236,942, which is a division of Ser. No. 658,789, Feb. 26, 1991, Pat. No. 5,100,906, which is a continuation-in-part of Ser. No. 513,524, Apr. 19, 1990, abandoned.

[51] Int. Cl.$^5$ ............................................. A61K 31/28
[52] U.S. Cl. ..................................................... 514/384
[58] Field of Search ......................................... 514/384

[56] References Cited

U.S. PATENT DOCUMENTS

| | | | |
|---|---|---|---|
| 4,732,900 | 3/1988 | Weber et al. | 514/255 |
| 4,775,688 | 10/1988 | Kane et al. | 514/384 |
| 4,847,276 | 7/1989 | Yarrington | 514/384 |
| 4,912,095 | 3/1990 | Kane et al. | 548/263.2 |

FOREIGN PATENT DOCUMENTS 280867  9/1988  European Pat. Off. .

OTHER PUBLICATIONS

G. Maffii, et al., *Il. Farmaco. Ed. Sci.*, 13, 629-38 (1958) (Translation provided).
J. P. Henichart, et al. *Mol. Pharmacol.*, 20(3), 598-601 (1981).
J. P. Henichart, et al. *Eur. J. Med. Chem.-Chim. Ther.*, 12(2), 117-2 (1977).
K. C. Joshi, et al. *J. Indian Chem. Soc.*, 51(6), 613-5 (1974).
J. M. Kane. *Synthesis* (10), 912-4 (1987).
J. M. Kane, M. W. Dudley, S. M. Sorenson, and F. P. Miller, *J. Med. Chem.* 31(6), 1253-8 (1988).
D. E. Sternberg, et al. *Archives of General Psychiatry, vol.* 33, No. 2, Feb. 1976 pp. 219-224.

Primary Examiner—Marianne M. Cintins
Assistant Examiner—T. J. Criares
Attorney, Agent, or Firm—Edlyn S. Simmons

[57] ABSTRACT

This invention relates to the enhancement of memory and cognition and the treatment of Alzheimer's disease and Wernicke-Korsakoff syndrome by administration of 5-($R_n$-phenyl)-4-alkyl-3H-1,2,4-triazole-3-thiones of the formula

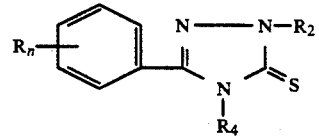

wherein
  R is halogen, trifluoromethyl, $C_{1-4}$ lower alkyl or $C_{1-4}$ lower alkoxy,
  n is zero, 1 or 2, and
  $R_2$ represents hydrogen or $C_{1-3}$ lower alkyl; and
  $R_4$ independently represents $C_{1-3}$ lower alkyl.

15 Claims, No Drawings

5-ARYL-4-ALKYL-3H-1,2,4-TRIAZOLE-3-THIONES USEFUL AS MEMORY ENHANCERS

This is a division of application Ser. No. 07/832,062, filed Feb. 6, 1992, now U.S. Pat. No. 5,236,942, which is a division of application Ser. No. 07/658,789, filed Feb. 26, 1991, now U.S. Pat. No. 5,100,906; which is a continuation-in-part of application Ser. No. 07/513,524, filed Apr. 19, 1990, now abandoned.

This invention relates to the use as enhancers of cognition and memory of 5-aryl-4-alkyl-3H-1,2,4-triazole-3-thiones.

More specifically, this invention relates the enhancement of memory and cognition and the treatment of Alzheimer's disease and Wernicke-Korsakoff syndrome by administration of compounds of the formula I and the pharmaceutically acceptable salts thereof

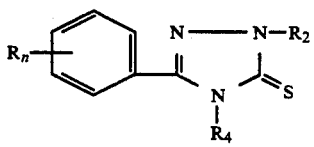

I wherein
R represents halogen, trifluoromethyl, $C_{1-4}$ lower alkyl or $C_{1-4}$ lower alkoxy, with n being zero, 1 or 2;
$R_2$ represents hydrogen or $C_{1-3}$ lower alkyl; and
$R_4$ represents $C_{1-3}$ lower alkyl.

BACKGROUND OF THE INVENTION

Memory is dependent upon the function of cholinergic cells in the cortex and hippocampus of the forebrain. The cholinergic cells in the basal forebrain reside in three regions, the nucleus basalis of Meynert, the medial septal nucleus and the nucleus of the diagonal band. These cells are responsible for most, perhaps all, of the cholinergic innervation in the cortex and hippocampus. It is known that these three structures and that their respective pathways are important in memory. Additionally, it is known that in Alzheimer's dementia up to half of these neurons and their projections may be lost. By stimulating the remaining neurons it should be possible to recover some of the memory deficits in Alzheimer's dementia and other forms of memory loss, including Wernicke-Korsakoff syndrome.

Previous reports have indicated that agents with activity at the γ-aminobutyric acid (GABA)-receptor complex when given in vivo modulate high affinity choline uptake (HACU) measured in vitro. It is thought that HACU measured in vitro reflects the activity of cholinergic neurons in vivo. Drugs which have a sedative or hypnotic activity have generally been found to depress cortical or hippocampal HACU. More recently, several studies, for example, those of Lorez, et al., *Drug Devel. Res.* 14, 359–362, 1988; Shih and Pugsley, *Life Sci.* 36, 2145–2152, 1985; Spignoli et al., *Clin. Neuropharmacol. Supp.* 3, 39–47, 1986; Nakahiro, M., et al., *Br. J. Pharmacol.* 95, 1303–1307, 1988, report that drugs which enhance cognition, e.g., pramiracetam, oxiracetam and pantoyl-GABA, stimulate cortical or hippocampal HACU after in vivo administration.

Another measure of cholinergic activity is the binding of the radioligand [$^3$H] hemicholinium-3, ([$^3$H] HC-3) which labels the carrier that mediates choline transport. Swarm and Hewitt (*Neuropharmacol.* 27:6117.615, 1988) have demonstrated that the $B_{max}$ of $^3$H HC-3 increases in parallel with HACU when cholinergic synaptosomes are stimulated. Therefore, the stimulation of [$^3$H] HC-3 binding in vitro after treatment with drugs in vivo is also a marker for increased cholinergic activity, predictive of enhanced cognition in treated animals.

Compounds of formula I wherein $R_2$ represents $C_{1-3}$ lower alkyl have previously been shown to have antidepressant activity, as disclosed, for example, in U.S. Pat. No. 4,775,688, issued Oct. 4, 1988, and in U.S. Pat. No. 4,912,095, issued Mar. 27, 1990. 5-(4-Chlorophenyl)-2,4-dimethyl-3H-1,2,4-triazole-3-thione, the compound of formula I wherein $R_2$ and $R_4$ both represent methyl, n is 1, and R represents chloro located in the 4-position of the phenyl substituent, is useful in the treatment of thrombocytosis and the prevention of thrombosis and hemorrhage resulting therefrom, as disclosed, for example, in U.S. Pat. No. 4,847,276, issued Jul. 11, 1989.

The effects of known antidepressant drugs on cholinergic markers for activity such as high affinity choline uptake (HACU) or [$^3$H] hemicholinium-3 binding is not consistent. Garattini et al. (*Psychopharmacol.* 82:210–214, 1983) reported a weak effect of minaprine on striatal, cortical and hippocampal HACU after a 30 mg/kg. acute dose. However, other antidepressants such as amitriptyline (Hridina and Elson-Hartman, *Neuropharmacol.* 21:1349–53, 1982; and Goldman and Erickson, *Neuropharmacol.* 22:1215–1222, 1983) and imipramine, desipramine, iprindole, and viloxazine (Jones, *Can. J. Physiol. Pharmacol.* 59:392–396, 1981) had no effect on HACU after acute administration i.p. Therefore we can conclude that stimulation of cortical markers for cholinergic activity are not generally increased by antidepressant drugs.

Long term potentiation in the hippocampus is also widely regarded as a useful model for the physiological processes underlying the development of memory. It is known that many compounds that are known to enhance memory also augment the development of this long term potentiation in the hippocampus. Unfortunately, most of the known memory enhancing compounds also produce side effects which limit their therapeutic potential. Such side effects are not found with compounds of formula I.

DETAILED DESCRIPTION OF THE INVENTION

In formula I, n is zero, representing an unsubstituted phenyl moiety, n is one, representing a mono-substituted phenyl moiety with the R-substitutent being a group located at any of the ortho, meta or para positions, or n is 2, representing a disubstituted phenyl moiety wherein substitution is in any of the 2,3-; 2,4-; 2,5-; 2,6-; 3,4-; and 3,5-positions. As used herein halogen represents chloro, fluoro or bromo. Preferably n is zero or 1. When n is 2, the groups represented by R may be the same or different. When n is 1 or 2, R preferably represents halogen, with fluoro being most preferred. When R represents $C_{1-4}$ alkyl or $C_{1-4}$ alkoxy, the alkyl moiety may be straight or branched. Preferably $R_2$ and $R_4$ represent methyl, but may independently represent any straight or branched $C_{1-3}$ alkyl group. When $R_2$ represents hydrogen, the tautomers of the compounds of formula I are also encompassed by this invention.

The pharmacological properties of these compounds as enhancers of memory and cognition and their relative potencies may be measured through their effect on neurotransmitters in the brain. Since drugs that block GABA inhibition in the cholinergic neurons of the basal forebrain nuclei will stimulate cholinergic firing, thus higher stimulating memory, the capacity of the drugs to enhance cognition can be assessed by measuring the increase in cholinergic firing rate. The increase in cholinergic firing rate is measured indirectly by measuring choline uptake or [$^3$H] hemicholinium-3 binding in brain cells taken from treated animals.

To test for [$^3$H] hemicholinium-3 binding in brain cells from the brain cortex, drugs were dissolved in saline by sonication. Male Sprague-Dawley rats were dosed i.p. and sacrificed by decapitation 60 min after injection. The brains were removed and dissected, and tissue was homogenized in 20 volumes of ice-cold buffer and stored frozen until assayed. Binding was measured by incubating the tissue with varying concentrations of [$^3$H]hemicholinium-3 in an isotonic Tris buffer (pH 7.4) for 60 min at room temperature. The incubation was terminated by rapid filtration through Whatman GF/B filters. After drying, the filters were placed in scintillation cocktail and radioactivity was determined using a Beckman scintillation counter. In two experiments, the values for the $K_d$ and $B_{max}$ were-determined by nonlinear curve-fitting and the average values for samples of 3 or more animals reported. As shown in the following table, compounds of formula I increased [$^3$H] hemicholinium-3 binding in brain cortex cells by from 35% to 109% over the binding seen when saline was administered as a control. This increase in $B_{max}$ is indicative of greatly enhanced cognition. of greatly enhanced cognition.

TABLE 1

3H HEMICHOLINIUM-3 BINDING IN RAT BRAIN MEMBRANES

| Treatment | $B_{max}$ ± SEM (fmol/mg Protein) | $K_d$ ± SEM (nM) | % Increase in $B_{max}$ |
|---|---|---|---|
| Saline (n = 8) | 9.7 ± 1.0 | 4.9 ± 1.4 | |
| 5-(3-Fluorophenyl)-2,4-dimethyl-3H-1,2,4-triazole-3-thione (1/mg/kg), (n = 4) | 20.3 ± 1.2 | 3.8 ± 0.6 | 109 |
| 5-(3-Fluorophenyl)-2,4-dimethyl-3H-1,2,4-triazole-3-thione (2.5/mg/kg), (n = 4) | 15.2 ± 3.0 | 6.5 ± 1.8 | 57 |
| Saline (n = 6) | 11.9 ± 2.2 | 1.3 ± 0.2 | |
| 5-Phenyl-2,4-dimethyl-3H-1,2,4-triazole-3-thione (5 mg/kg), (n = 7) | 19.0 ± 3.4 | 2.8 ± 0.5 | 60 |
| 5-Phenyl-4-methyl-3H-1,2,4-triazole-3-thione (25 mg/kg), (n = 3) | 18.7 ± 3.2 | 2.14 ± 0.7 | 57 |
| 5-(3-Trifluoromethylphenyl)-2,4-dimethyl-3H-1,2,4-triazole-3-thione (25 mg/kg), (n = 3) | 16.0 ± 3.0 | 1.5 ± 0.1 | 35 |

Experiments also compared 5-(3-fluorophenyl)-2,4-dimethyl-3H-1,2,4-triazole-3-thione, a compound of formula I, with a series of β-carbolines in an electrophysiological assay system involving long term potentiation of the hippocampal slice. It was found that the β-carbolines, which act as inverse agonists at the benzodiazepine receptor and which have been shown to improve memory in animal learning and memory tests, produced an increase in the basal population spike amplitude and an increase in the magnitude of the long term potentiation. In these tests methyl 6,7-dimethoxy-4-ethyl-β-carboline-3-carboxylate, methyl β-carboline-3-carboxylate, and ethyl β-carboline-3-carboxylate were full inverse agonists and N-methyl-β-carboline-3-carboxamide was a partial inverse agonist. At higher concentrations these compounds produced epileptiform activity in the hippocampal slice consistent with their high dose convulsant properties. 5-(3-Fluorophenyl)-2,4-dimethyl-3H-1,2,4-triazole-3-thione produced effects on the basal population spike amplitude and on long term potentiation which were similar to those seen for the β-carbolines, indicating that this compound also has memory enhancing properties. Unlike the β-carbolines, however, high doses of 5-(3-fluorophenyl)-2,4-dimethyl-$^3$H-1,2,4-triazole-3-thione did not produce the epileptiform activity seen with the β-carbolines, indicating that compounds of formula I will not have the high dose convulsant profile of the β-carbolines.

The activity of these compounds in enhancing memory can also be confirmed in experiments that study working memory in rats by evaluating the acquisition of alternation behavior in a T-maze. The maze used has the shape of a T with alleys 16 cm wide and side walls 20 cm high, the main arm being 65 cm long and the two side arms 45 cm long. Male Sprague-Dawley rats are maintained on a 23 hour food deprivation schedule and are tested each day (Monday-Friday), each trial in the maze consisting of two runs. The rat starts at the end of the main arm and runs to the choice point where it must turn either left or right. The first is a forced run where one arm of the T-maze has been blocked off at the choice point. The remaining arm has a bowl of sweetened condensed milk as reward. On the second run the rat has a free choice of arms and learns by experience that food reward is to be found down the arm not visited on the first run. Trials are run at 30-second intervals, and the arm choice on the forced run is varied at random between trials. Arm entry is defined by the rat's placing all four paws in the arm, and incorrect selection of the arm is scored as an error. Noncompleted trials, where the rat has not made a choice within 3 minutes, are included as errors. 5-(3-Fluorophenyl)-2,4-dimethyl-3H-1,2,4-triazole-3-thione is administered one hour before the first trial of each session. Impairment of performance is achieved for testing the compound of this invention in two different ways.

TABLE 2

Incorrect Responses in the T-maze by Rats Treated with Scopolamine

| Treatment | Number of errors (12 = chance response) |
|---|---|
| Saline | 2.4 ± 0.7 |
| Scopolamine, 0.15 mg/kg | 6.9 ± 0.7** |
| Scopolamine, 0.15 mg/kg 5-(3-Fluorophenyl)-2,4-dimethyl-3H-1,2,4-triazole-3-thione, 1 mg/kg | 5.0 ± 0.26* |
| Scopolamine, 0.15 mg/kg 5-(3-Fluorophenyl)-2,4-dimethyl-3H-1,2,4-triazole-3-thione, 5 mg/kg | 3.0 ± 0.8 |

*p<0.05 vs saline (ANOVA and Mann-Whitney U-Test)
**p<0.01 vs saline (ANOVA and Mann-Whitney U-Test)
p<0.05 vs scopolamine (ANOVA and Mann-Whitney U-Test)

In the trials summarized in Table 2, the amnestic muscarinic antagonist scopolamine is administered subcutaneously at a dose of 0.15 mg/kg 15-minutes before the first trial, and there is a delay of 5–10 seconds after the forced run before the second run of the trial. Table 2 shows the number of incorrect responses in 24 trials of rats treated with scopolamine. All values are expressed as the mean number of errors per block of twenty-four trials with groups of 12 animals ± the standard error of the mean. For this test, the number of errors expected by random response, i.e., the selection of the correct arm 50% of the time, is 12. The data in Table 2 show that 5-(3-fluorophenyl)-2,4-dimethyl-3H-1,2,4-triazole-3-thione reverses the scopolamine-induced memory deficit in the T-maze at the 5 mg/kg dose.

TABLE 3

Incorrect Responses in the T-maze by Rats After 60-Second Delay

| Dose 5-(3-Fluorophenyl)-2,4-dimethyl-3H-1,2,4-triazole-3-thione | Number of errors (5 = chance response) | |
|---|---|---|
| | 0-Second Delay | 60-Second Delay |
| Saline | 0.83 ± 0.21 | 4.17 ± 0.53* |
| 1 mg/kg | 0.50 ± 0.26 | 4.42 ± 0.47* |
| 5 mg/kg | 0.67 ± 0.33 | 2.33 ± 0.50* |
| 10 mg/kg | 0.58 ± 0.19 | 1.75 ± 0.43 |

*$p < 0.05$ vs 0-seconds delay (ANOVA and Wilcoxin Test)

Table 3 shows the result of trials wherein memory is impaired by increasing the delay between the first and second runs from 0-seconds to 60 seconds. The table compares the number of incorrect responses by rats tested in trials wherein there is no delay after the forced run and trials wherein there is a 60-second delay. All values are expressed as the mean number of errors per block of ten trials with groups of 12 animals ± the standard error of the mean. For this test, the number of errors expected by random response, i.e., the selection of the correct arm 50% of the time, is 5. These results show that 5-(3-fluorophenyl)-2,4-dimethyl-3H-1,2,4-triazole-3-thione effectively reverses the time dependent deficit in this maze test and is therefore effective in improving memory in young, healthy rats as well as in the scopolamine-treated memory-impaired rats.

Compounds of formula I can be administered to mammalian patients, including humans, afflicted with cognitive disorders such as Alzheimer's disease and other forms of memory loss. In addition to Alzheimer's disease, other types of dementia that display cholinergic deficits may be ameliorated by compounds of formula I. For example, Wernicke-Korsakoff syndrome, a form of dementia resulting from alcoholism, can also be treated by administration of a compound of formula I. Arendt, et al., *Acta Neuropathologica* 61:101-108, 1983, have found indications that some patients with Wernicke-Korsakoff syndrome have significant loss of cholinergic neurons in the basal forebrain in addition to adrenergic deficits.

In general, normal aging may result in a generalized deficit in cholinergic function even in the absence of dementia. Sherman, et al., *Neurobiol Aging* 2:99-104, 1981, found choline uptake in aged (23-26 month old) rats to be decreased by 22% when compared to young adult rats (6 months old). This decrease in cholinergic activity was observed without any concomitant loss of cholinergic neuron number. Animal research suggests that enhancement of memory may be possible in non-demented individuals as well. Micheau, et al., *Pharmacol. Biochem. Behar.* 23:195-198, 1985, found that in mice trained in an operant conditioning memory task, performance was enhanced in mice treated with sulbutiamine, which increased hippocampal high affinity choline uptake, versus normal vehicle-treated control mice. Indeed, mice trained in several different memory paradigms exhibit an increase in high affinity choline uptake in cortex and hippocampus, as shown by Toumane, et al., *Behav. Brain Res.* 30:225-234, 1988, suggesting that such an increase in cholinergic activity in these regions is a normal part of memory formation. Treatment of normal aged individuals with a compound of formula I will enhance memory by counteracting the cholinergic deficit that interferes with learning.

For oral administration, the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose or cornstarch. In another embodiment, the compounds of general formula I can be tableted with conventional tablet bases such as lactose, sucrose and cornstarch, in combination with binders, such as acacia, cornstarch or gelatin, disintegrating agents such as potato starch or alginic acid, and a lubricant such as stearic acid or magnesium stearate.

For patenfetal administration, the compounds may be administered as injectable dosages of a solution or suspension of the compound in a physiologically acceptable diluent with a pharmaceutical carrier which can be a sterile liquid such as water, alcohols, oils and other acceptable organic solvents, with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol, or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert material such as biodegradable polymers or synthetic silicones, for example Silastic ®, a silicone rubber manufactured by the Dow-Corning Corporation.

As is true in many classes of compounds generally suitable for any particular pharmacological activity having a therapeutic end-use application, certain subgeneric groups and certain specific members of the class are preferred because of their overall therapeutic index and their biochemical and pharmacological profile. In this instance the preferred compounds are those wherein both $R_2$ and $R_4$ groups are methyl, and those wherein the R substituent is fluoro. Specifically preferred compounds are 5-(3-fluorophenyl)-2,4-dimethyl-3H-1,2,4-triazole-3-thione and 5-phenyl-2,4-dimethyl-3H-1,2,4-triazole-3-thione.

The compounds of formula I may readily be prepared using processes and procedures analogously known in the art as seen by the following reaction scheme.

REACTION SCHEME

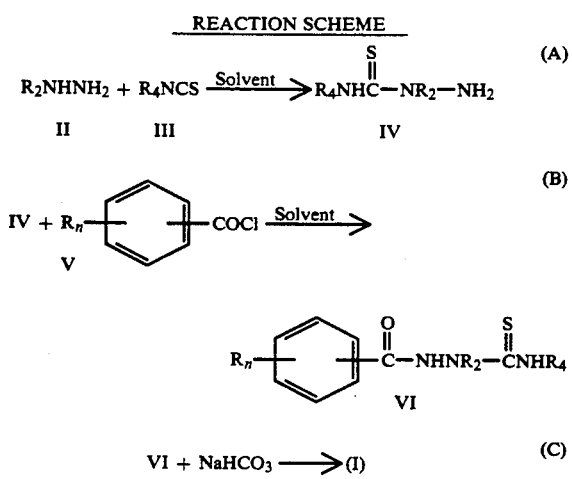

(C) VI + NaHCO₃ ⟶ (I)

wherein $R_2$, $R_4$, n and R are as previously defined.

In step A, the preparation of the thiosemicarbazides (IV) is readily effected by reacting hydrazine (II) with an isothiocyanate (III) by contacting the reactants in a suitable solvent. The reaction is quite rapid and may be carried out at 0° C. to room temperature. Although the reaction proceeds rapidly, the mixture may be left for up to hours without significant decrease in yields. Reflux conditions may be employed but are not preferred. Almost all solvents (with the exception of water and organic acids) may be used. Anhydrous alcohols (preferably ethanol or methanol) are preferred although dimethylformamide (DMF), CHCl₃, CH₂Cl₂, tetrahydrofuran (THF) and Et₂O may also be used. The required hydrazines and isothiocyanates are usually commercially available, but may be prepared by known techniques.

In Step B, the desired substituted benzoyl thiosemicarbazides (VI) may be prepared by reacting the thiosemicarbazides (IV) with an $R_n$-substituted benzoyl chloride (V) in an aprotic solvent such as pyridine, CHCl₃, THF or the like. The acylation proceeds rather easily at temperatures ranging from 0° C. to room temperature over periods of 3 to 24 hours, although elevated temperatures (e.g. reflux temperatures) may be employed. Again, the acid halides (V) generally are commercially available but may also be prepared from the corresponding acids which are generally commercially available.

In Step C, the substituted benzoyl thiosemicarbazides (VI) are subjected to a cyclization reaction which is effected by heating the compounds (VI) in an aqueous base, e.g. sodium bicarbonate or sodium hydroxide. Alcoholic bases may be utilized, but generally are less desirable. The reaction is conducted at about the reflux temperature of the solvent, preferably at about 65°–100° C. In practice, the thiosemicarbazides (VI) need not be purified for use in Step C so that even 1:1 mixtures with pyridine hydrochloride, produced as a by-product when pyridine is employed as a solvent in Step B, may be used.

The following specific examples are given to illustrate the preparation of the compounds of this invention although the scope of compounds exemplified is not meant to be limiting.

Preparation of $R_2,R_4$-Substituted-Thiosemicarbazides

EXAMPLE 1

2,4-Dimethylthiosemicarbazide

To a stirred solution of methyl hydrazine (16.0 ml, $3.00 \times 10^{-1}$ mole) and sieve dry ethanol (50 ml) was added dropwise a solution of methyl isothiocyanate (22.0 g, $3.00 \times 10^{-1}$ mole) and sieve dry ethanol (30 ml). The reaction was exothermic and gently refluxed as the isothiocyanate was added. A precipitate soon formed. After stirring overnight, the reaction was cooled in an ice bath. The precipitate was then collected by filtration, washed with a little cold isopropanol, and dried by suction, affording a colorless solid: 26.7 g (75%). This material was crystallized two times from water and two times from isopropanol, affording small colorless needles: 14.7 g (41%), mp 135°–137° C.

Preparation of 1-$R_n$-Benzoyl)-$R_2,R_4$-Substituted Thiosemicarbazides

EXAMPLE 2

1-(4-Chlorobenzoyl)-2,4-dimethylthiosemicarbazide

To a stirred solution of 2,4-dimethylthiosemicarbazide (1.19 g, $1.00 \times 10^{-2}$ mole) and pyridine (10 ml) was added dropwise 4-chlorobenzoyl chloride (1.3 ml, $1.02 \times 10^{-2}$ mole). The reaction turns yellow and a mild exotherm is noted. After stirring overnight the reaction was evaporated to dryness affording a beige solid: 3.61 g (97%) which represents a mixture of the desired 1-(4-chlorobenzoyl)-2,4-dimethylthiosemicarbazide and pyridine hydrochloride. In general this mixture was used without further purification in the subsequent cyclization step. If pure 1-(4-chlorobenzoyl)-2,4-dimethylthiosemicarbazide is desired, the above mixture is treated with water and that which does not dissolve is collected by filtration. After drying by suction this material is crystallized from ethanol affording colorless matted needles: 1.03 g (40%), mp=206°–208° C. (decomp).

Preparation of Final Products

EXAMPLE 3

5-(4-Chlorophenyl)-2,4-dimethyl-3H-1,2,4-triazole-3-thione

The 1:1 mixture of 1-(4-chlorobenzoyl)-2,4-dimethylthiosemicarbazide and pyridine hydrochloride (3.61 g of mixture) from Example 2 and 1 molar aqueous NaHCO₃ (100 ml, $1.00 \times 10^{-1}$ mole) were stirred and warmed to reflux. After refluxing for 5 hours the reaction was allowed to cool. It was then placed in a refrigerator for several hours before the precipitate was collected by filtration. The collected material was dried partially by suction before being transferred to a desiccator where it was dried at high vacuum. This affords the desired product as a beige powder: 2.01 g (84%). This was purified by flash chromatography and subsequent crystallization from isopropanol yielding small, slightly yellowish plates: 1.74 g (73%), mp 113°–115° C.

In a similar manner, by substituting a variety of substituted benzoyl chlorides and a variety of 4-substituted thiosemicarbazides for the reactants of examples 1–3 and by substantially following the techniques therein, the following compounds are readily prepared.

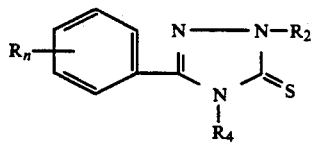

| $R_n$ | $R_2$ | $R_4$ | M.P. °C. |
|---|---|---|---|
| 4-F | H | $CH_3$ | 207–209° |
| 4-F | $CH_3$ | $CH_3$ | 130–132° |
| 2-F | $CH_3$ | $CH_3$ | 106–108° |
| 2-F | H | $CH_3$ | 137–139° |
| 2-F | H | $C_2H_5$ | 138–140° |
| 3-F | $CH_3$ | $CH_3$ | 126–128° |
| 2,4-$F_2$ | $CH_3$ | $CH_3$ | 102–104° |
| 2,6-$F_2$ | $CH_3$ | $CH_3$ | 158–160° |
| 4-Cl | $CH_3$ | $C_2H_5$ | 113–115° |
| 4-Cl | H | $CH_3$ | 204–206° |
| 4-Cl | $C_2H_5$ | $CH_3$ | 118–120° |
| 4-Cl | $C_2H_5$ | $C_2H_5$ | 91–93° |
| 2-Cl | $CH_3$ | $CH_3$ | 138–140° |
| 4-Cl | H | $CH_3$ | 210–212° |
| 4-Cl | $CH_3$ | $CH_3$ | 114–116° |
| 4-Cl | $CH_3$ | n-$C_3H_7$ | B.P. 240–250° 0.55 mm Hg |
| 2,4-$Cl_2$ | $CH_3$ | $CH_3$ | 135–137° |
| 3,4-$Cl_2$ | $CH_3$ | $CH_3$ | 161–163° |
| 2,6-$Cl_2$ | $CH_3$ | $CH_3$ | 115–116° |
| — | H | $CH_3$ | 164–166° |
| — | $CH_3$ | $CH_3$ | 134–135° |
| — | $C_2H_5$ | $CH_3$ | 105–107° |
| — | $CH_3$ | $C_2H_5$ | B.P. 388° 746 mm Hg |
| 4-$CH_3$ | $CH_3$ | $CH_3$ | 94–96° |
| 4-$CH_3$ | H | $CH_3$ | 201–203° |
| 4-t-$C_4H_9$ | $CH_3$ | $CH_3$ | 160–162° |
| 2-$CH_3O$ | $CH_3$ | $CH_3$ | 110–112° |
| 4-$CH_3O$ | $CH_3$ | $CH_3$ | 96–98° |
| 4-$CH_3O$ | H | $CH_3$ | 172–174° |
| 2-$C_4H_9O$, 3$CH_3O$ | $CH_3$ | $CH_3$ | 95–97° |
| 3-$CF_3$ | $CH_3$ | $CH_3$ | 73–75° |

What is claimed is:

1. A method for the enhancement of memory and cognition which comprises administering to a patient in need thereof an effective dose of a compound of the formula

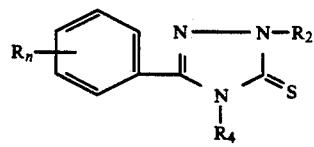

wherein
R is halogen, trifluoromethyl, $C_{1-4}$ lower alkyl or $C_{1-4}$ lower alkoxy;
n is zero, 1 or 2;
$R_2$ represents hydrogen or $C_{1-3}$ lower alkyl; and
$R_4$ independently represents $C_{1-3}$ lower alkyl.

2. A method of claim 1 wherein R is halogen.
3. A method of claim 2 wherein R is fluoro.
4. A method of claim 1 wherein n is one.
5. A method of claim 1 wherein n is two.
6. A method compound of claim 1 wherein n is zero.
7. A method compound of claim 1 wherein $R_2$ and $R_4$ each are methyl.
8. A compound of claim 7 wherein R is fluoro and n is one.
9. A method of claim 1, said compound being 5-(3-fluorophenyl)-2,4-dimethyl-3H-1,2,4-triazole-3-thione.
10. A method of claim 1, said compound being 5-(2,4-difluorophenyl)-2,4-dimethyl-3H-1,2,4-triazole-3-thione.
11. A method of claim 1, said compound being 5-(4-fluorophenyl)-2,4-dimethyl-3H-1,2,4-triazole-3-thione.
12. A method of claim 1, said compound being 5-(2-fluorophenyl)-2,4-dimethyl-3H-1,2,4-triazole-3-thione.
13. A method of claim 1, said compound being 5-phenyl-4-dimethyl-3H-1,2,4-triazole-3-thione.
14. A method of claim 1, said compound being 5-phenyl-4-methyl-3H-1,2,4-triazole-3-thione.
15. A method of claim 1, said compound being 5-(2,6-difluorophenyl)-2,4-dimethyl-3H-1,2,4-triazole-3-thione.

* * * * *